United States Patent [19]

Nair

[11] Patent Number: 5,073,554
[45] Date of Patent: Dec. 17, 1991

[54] TWO NON-POLYGLUTAMATABLE ANTIFOLATES

[76] Inventor: Madhavan G. Nair, 7005 Charleston Oaks Dr. N., Mobile, Ala. 36695

[21] Appl. No.: 562,673

[22] Filed: Aug. 3, 1990

Related U.S. Application Data

[63] Continuation-in-part of Ser. No. 467,025, Jan. 18, 1990, Pat. No. 4,996,207.

[51] Int. Cl.$^5$ ............................................. A61K 31/505
[52] U.S. Cl. ...................................... 514/249; 544/260
[58] Field of Search .......................... 514/249; 544/260

[56] References Cited

U.S. PATENT DOCUMENTS

| | | | |
|---|---|---|---|
| 4,369,319 | 1/1983 | DeGraw et al. | 544/260 |
| 4,532,241 | 7/1985 | DeGraw et al. | 514/258 |
| 4,628,090 | 12/1986 | Coward | 544/260 |
| 4,996,207 | 2/1991 | Nair et al. | 544/260 |

FOREIGN PATENT DOCUMENTS 0081385  4/1987  Japan ................................. 544/260

OTHER PUBLICATIONS

Baugh, Krumdieck, Nair, Polyglutamyl–Methotrexate, BBRC 52, 27, 73.
Abraham, Nair, Kisliuk, et al., Folate Analogues–J. Med. Ch. 33, 711, 90.
Kumar, Kisliuk, Gaumont et al., Inhibition of–Biochem, Pharmacol. 38, 541, 1989.
Ueda, Dutschman, Nair et al., Inhibitory Action–Molec. Pharmacol. 30, 149, 1986.
Vidal-Cros et al., Jour. Org. Chem. vol. 50, 3163–3167 (1985).
Nair, M. Jour. Org. Chem., vol. 50, pp. 1879–1884 (1985).
DeGraw, Jour. Med. Chem. vol. 17, pp. 552–553 (1974).
Chem. Abstract, vol. 114, No. 7 Entry 62056d, abstracting Abraham et al., J. Med. Chem., vol. 34, No. 1, pp. 222–227 (1991).

*Primary Examiner*—Donald G. Daus

[57] ABSTRACT

Two new non-polyglutamatable glutamic acid derivatives in the antifolate series are provided as well as procedures for their preparation. These compounds are: 4-amino-4-deoxy-10-methylpteroyl-$\tau$-methyleneglutamic acid (1) and 4-amino-4-deoxy-10-methylpteroyl-$\beta$-hydroxyglutamic acid (2). Compounds 1 and 2 do not undergo polyglutamylation as determined by their inability to serve as substrates for folylpolyglutamate synthetase (FPGS), and they are powerful inhibitors of human dihydrofolate reductase (DHFR). Both compounds 1 and 2 are powerful inhibitors of the growth of Manca human lymphoma, human leukemia (CCRF-CEM) and H35 hepatoma cells.

6 Claims, No Drawings

TWO NON-POLYGLUTAMATABLE ANTIFOLATES

ORIGIN OF INVENTION

The invention described herein was in part made in the course of work under a grant from the National Institutes of Health, Department of Health, Education and Welfare.

RELATED U.S. APPLICATION DATA

Continuation-in-part of Ser. No. 07/467,025; Jan. 18, 1990, now U.S. Pat. No. 4,996,207.

The process of this invention is illustrated by the reaction sequence depicted in Schemes 1, and 2 where the compound numbers identify the same compounds which they identify in all descriptions.

USE ADVANTAGE

The most widely used antifolate drug for the treatment of human cancers is methotrexate (MTX). Recently 10-ethyl-10-deazaaminopterin (10-EDAM), which is an analogue of methotrexate, has been shown to exhibit a wide spectrum of antitumor activity. Both MTX and 10-EDAM are metabolized to their poly-$\tau$-glutamyl derivatives. The target enzyme for both antifolates (MTX and 10-EDAM) is dihydrofolate reductase. 10-EDAM has the additional advantage of enhanced transport to mammalian cells compared to MTX. The polyglutamyl metabolites of MTX and 10-EDAM inhibit other folate-based enzymes in addition to dihydrofolate reductase. Therefore, antifolate polyglutamylation results in the potentiation of cytotoxicity and undoubtedly contributes to the undesirable toxic side effects of the drugs because of the accumulation of these toxic metabolites and their prolonged retention in normal proliferative tissues such as liver, kidney, intestinal epithelium and bone marrow.

Any classical antifolate that has biochemical properties similar to methotrexate (such as dihydrofolate reductase inhibition and inhibition of tumor cell growth), but which is incapable of polyglutamylation should show remarkably less host toxicity. Compounds 1 and 2 show dihydrofolate reductase inhibition similar to that of methotrexate. Antifolates 1 is transported to tumor cells more efficiently than methotrexate. On a comparative basis, 1 and 2 are nearly as powerful as methotrexate in inhibiting the growth of a number of tumor cells. Neither of the new antifolates (1 or 2) is a substrate for folylpolyglutamate synthetase and therefore they cannot be metabolized to poly-$\tau$-glutamates. In accordance with the invention it was determined that compounds 1 and 2 are new and novel non-polyglutamatable and relatively nontoxic antifolates that should be useful in the treatment of human cancers and they are immune suppressants with activity similar to that of methotrexate. The dose is 0.1–500 mg daily in humans parenterally or orally.

BACKGROUND OF THE INVENTION

1. Field of the Invention

This invention relates to anticancer agents and the processes for their manufacture.

Cancer is an acute or chronic disease of man which is characterized by abnormal tissue growth and destruction that can be effectively treated with anticancer drugs such as methotrexate.

In Biochemical and Biophysical Research Communications 52:27 (1973), Baugh, Krumdieck and Nair reported on the metabolism of the well known anticancer drug methotrexate to its poly-$\tau$-glutamates in human tissues. Nair and Baugh in Biochemistry 12:3923 (1973) reported the chemical synthesis of the poly-$\tau$-glutamyl metabolites of methotrexate, the formation of these metabolites in rodent tissues, and the hydrolytic susceptibility of these metabolites to the enzyme "conjugase," derived from hog kidney and human plasma. Methotrexate polyglutamates are relevant to cancer chemotherapy because their formation is related to toxicity; they efflux from the cell at a slower rate than methotrexate and they are more inhibitory to thymidylate synthase and AICAR transformylase.

Continuing work with other antifolates led to the discovery that, like methotrexate, many antifolates undergo polyglutamylation. In 1988, Nair, Nanavati, Gaumont and Kisliuk reported in the Journal of Medicinal Chemistry that, like methotrexate, 10-deazaaminopterin and its 10-ethyl derivative undergo polyglutamylation (J. Med. Chem. 31:181, 1988) and these polyglutamyl derivatives inhibit the enzyme thymidylate synthase more effectively than the parent compound. The potent antileukemic agent $N^{10}$-propargyl-5,8-dideazafolic acid (CB 3717, PDDF) is converted to its polyglutamyl derivatives in normal murine tissues (M. G. Nair, Mehtha and I. G. Nair, Fed. Proc. 45:821, 1986). Nair, Nanavati, Kisliuk, Gaumont, Hsio and Kalman reported in the Journal of Medicinal Chemistry (29:1754, 1986) that the polyglutamyl derivatives of PDDF are more effective in inhibiting thymidylate synthetase.

Cheng, Dutschman, Starnes, Fisher, Nanavati and Nair in Cancer Research (34:598, 1985) and Ueda, Dutschman, Nair, DeGraw, Sirotnak and Cheng in Molecular Pharmacology (30:149, 1986) reported that the polyglutamyl derivatives of PDDF and 10-deazaaminopterin were more inhibitory to human thymidylate synthase than the non-polyglutamylated parent compounds. The antipurine effect of the well-known anticancer and anti-arthritic drug methotrexate has been attributed to its polyglutamyl derivatives inhibiting the enzyme AICAR transformylase (Allegra, Drake, Jolivet and Chabner, Proc. Nat. Acad. Sci. USA 82:4881, 1985). These data taken together clearly show that the toxicity of classical antifolates like methotrexate, 10-deazaaminopterins and PDDF is potentiated by polyglutamylation. The accumulation of their toxic metabolites in normal human tissues such as kidneys, bone marrow and liver undoubtedly contributes to the undesirable side effects of these drugs and seriously undermines their clinical utility.

Therefore, it was of interest to us to develop classical antifolates that are powerful inhibitors of the target enzyme dihydrofolate reductase, but incapable of elaboration in vivo to their polyglutamyl derivatives. If these compounds are transported as efficiently as methotrexate to tumor cells, then such compounds should have clinical utility as anticancer drugs and exhibit lower host toxicity. Compounds 1 and 2 have shown excellent antitumor activity in three tumor models (Table I). Both compounds were similar to methotrexate in their efficacy in inhibiting the target enzyme dihydrofolate reductase (Table II). As shown in Table III, compound 1 is transported more efficiently to H35 hepatoma cells than methotrexate as determined by its ability to compete with folinic acid transport in this cell line.

Compounds 1 and 2 were evaluated as substrates and inhibitors of purified human leukemia cell folypolyglutamate synthetase (FPGS). It has been established that substrates of FPGS are capable of polyglutamylation in vivo and the relative magnitude of substrate activity of an antifolate to this enzyme compared to a standard is a measure of its relative ability to undergo polyglutamylation in vivo. In table IV, the relative substrate activities of compounds 1 and 2 are presented compared to two standards, aminopterin and 10-deazaaminopterin. The data establish that the new compounds 1 and 2 are not substrates of CCRF-CEM human leukemia cell folylpolyglutamate synthetase.

Therefore, by analogy to methotrexate, compounds 1 and 2 should have clinical utility as novel anticancer drugs capable of exhibiting lower host toxicity. In addition, they should be useful in the treatment of rheumatoid arthritis since they are expected to be immune suppressants to a similar degree as methotrexate.

This invention accordingly also provides a process for treating leukemia, ascitic and solid tumors and rheumatoid arthritis which comprises administering to a warm-blooded animal with an abnormal proportion of leukocytes or other evidence of malignancy or rheumatoid arthritis a therapeutic nontoxic amount of compounds 1 and 2 as such, or in the form of a pharmacologically acceptable salt thereof.

The process of the invention for the preparation of 4-amino-4-deoxy-10-methylpteroyl-$\tau$-methyleneglutamic acid (1) is a synthesis in which commercially available 4-amino-4-deoxy-10-methylpteroic acid (3) is coupled with diethyl-$\tau$-methylene glutamate (5) followed by base hydrolysis (Scheme 1). Likewise, the process of the invention for the preparation of 4-amino-4-deoxy-10-methylpteroyl-3-hydroxyglutamic acid (2) is a synthesis in which 4-amino-4-deoxy-10-methylpteroic acid is coupled with dimethyl-3-hydroxyglutamate followed by base hydrolysis (Scheme 2).

Stage I (Scheme 1) is essentially the conversion of 4-amino-4-deoxy-10-methylpteroic acid (3) to the corresponding mixed anhydride (4) by treatment with an equal amount of alkylchloroformate such as isobutylchloroformate in an appropriate solvent such as dimethylsulfoxide (DMSO) in the presence of an acid acceptor, preferably a tertiary amine such as triethylamine or N-methylmorpholine. This reaction can be carried out within a temperature range of 0°-30° C. Other acid acceptors such as substituted pyridines, tributylamine, collidine, lutidine or MgO may be substituted for triethylamine. The reaction may be conducted with other alkylchloroformates such as methyl, ethyl, propyl, etc. Other solvents such as dimethylformamide, hexamethylphosphoramide or dimethylacetamide may be used for this reaction.

In stage II the mixed anhydride 4 is reacted with an excess amount of a diester of $\tau$-methyleneglutamic acid such as diethyl-$\tau$-methyleneglutamic acid (5). Dimethyl, dibenzyl or di-t-butyl-$\tau$-methylene glutamic acid may be substituted for the diethyl derivative. Diethyl-$\tau$-methylene glutamate may be added as the hydrochloride form to the mixed anhydride solution 4 followed by the addition of an equal amount or an excess of an acid acceptor such as triethylamine. Alternatively, diethyl-$\tau$-methyleneglutamate hydrochloride may be dissolved in a suitable solvent such as DMF, neutralized with an equivalent amount of the acid acceptor, and then added to the mixed anhydride solution 4. This reaction mixture is stirred for 18 hours at 25°-30° C. and the solvent is removed by evaporation under reduced pressure. The resulting coupled product is stirred with an excess of a mixture of 0.1N NaOH and acetonitrile for 18 hours to give the target compound 1. The glutamic acid derivative 1 is soluble in alkali and can be isolated as a precipitate by the addition of an acid to the basic hydrolysate. The precipitate can be recovered by filtration, washed and dried.

For the preparation of compound 2 (Scheme 2), the solution of the mixed anhydride 4 is reacted with an excess amount of the diester of 3-hydroxyglutamic acid such as dimethyl-3-hydroxyglutamate (6). Diethyl, dibenzyl or di-t-butyl-3-hydroxyglutamate may be substituted for the dimethyl derivative. Dimethyl-3-hydroxyglutamate (6) may be added to the solution of the mixed anhydride as the hydrochloride followed by the addition of an equivalent or excess amount of the acid acceptor such as triethylamine. Alternatively, dimethyl-3-hydroxyglutamate hydrochloride may be dissolved in a suitable solvent such as DMF, neutralized with an equivalent amount of the acid acceptor such as triethylamine or N-methylmorpholine and then added to the mixed anhydride solution. The reaction mixture is then stirred for 18-24 hours at 25°-30° C. and the solvent is removed by rotary evaporation under reduced pressure. The resulting product is stirred with an excess of a 3:1 mixture of 0.1N NaOH:acetonitrile for 10-18 hours to give target compound 2. Compound 2 is soluble in alkali and it can be isolated as a precipitate by addition of an acid such as glacial acetic acid to the hydrolysate. The precipitate can be recovered by filtration, washed and dried.

The following examples illustrate application of the synthesis to the preparation of $\tau$-methyleneglutamic acid derivative 1 and 3-hydroxyglutamic acid derivative 2.

EXAMPLE I

Diethyl-$\tau$-methyleneglutamate hydrochloride $\tau$-Methyleneglutamic acid was purchased from Cal-BiochemBehring. In a round bottomed flask, 795 mg (5 mmol) of the above $\tau$-methyleneglutamic acid was dissolved in 25 ml of absolute ethyl alcohol. The solution was cooled to 0° C. in an ice bath, and 3 ml of thionyl chloride was slowly added while stirring. After the addition was complete, the reaction mixture was allowed to stir for 18 hours at 25° C., then refluxed for four hours and evaporated until a semi solid was obtained. Upon trituration with 40 ml of diethyl ether, diethyl-$\tau$-methyleneglutamate crystallized as a white solid: mp 87°-89° C.; mass spectrum (FAB) m/z, 217 (MH+); yield 1.0 g (80%).

4-Amino-4-deoxy-10-methylpteroyl-$\tau$-methyleneglutamic acid (1)

A solution of 326 mg (1 mmol) of 4-amino-4-deoxy-10-methylpteroic acid purchased from Aldrich Chemical Co. in a mixture of 5 ml of dimethyl sulfoxide (DMSO) and 35 ml of dimethylformamide (DMF) was prepared by the addition of 0.28 ml (2 mmol) of triethylamine and warming the mixture to 80°-90° C. The solution was then cooled to $-5°$ C. with the aid of an ice bath, and 0.262 ml (2 mmol) of freshly distilled isobutylchloroformate was added while stirring. After 15 minutes, the ice bath was removed and the reaction mixture was allowed to warm to 25° C. and kept for 30 minutes to complete the formation of the mixed anhydride 4. To this mixed anhydride solution was added 503 mg (2 mmol) of diethyl-γ-methyleneglutamate hydrochloride immediately followed by the addition of 0.28 ml (2 mmol) of triethylamine. The resultant reaction mixture was stirred for 18 hours at 25°-30° C., evaporated to dryness under reduced pressure at 70° C., triturated with 50 g of crushed ice, and filtered. The precipitate was stirred with a mixture of 50 ml of 0.1N NaOH and 15 ml of acetonitrile for 18 hours, when a clear solution was obtained. The pH of this solution was adjusted to 7.5 with 1N HCl, concentrated by rotary evaporation to ~20 ml, cooled and acidified with glacial acetic acid to pH 4.0. The resulting orange precipitate was filtered, washed and dried. HPLC analysis established that the product was a mixture of unreacted 4-amino-4-deoxy-10-methylpteroic acid (3) and the desired 4-amino-4-deoxy-10-methylpteroyl-γ-methylene glutamic acid (1) in a ratio of 1.0 to 2.0.

The target compound 1 was separated from this mixture by dissolving the crude product (350 mg) in 10 ml of 5% ammonium hydroxide solution and evaporating the solvent by rotary evaporation under reduced pressure. The ammonium salt thus obtained was dissolved in 15 ml of distilled water and applied on a column of 25 g of C18 silica gel equilibrated with 10% acetonitrile in water. The column was eluted with 10% acetonitrile in water and 5 ml fractions were collected. Fractions corresponding to the fast moving band on the column were pooled and acidified with glacial acetic acid to obtain a bright orange precipitate which was filtered, washed with distilled water and dried: yield, 177 mg (38%); mp>300° C. This compound gave the following analytical data consistent with the structure.

| Mol formula | Mol wt (calcd) | (found) | 0.1 N NaOH max nm |
|---|---|---|---|
| $C_{21}H_{22}N_8O_5$ | 466 | 466 | 256<br>371 |

EXAMPLE II

Dimethyl-3-hydroxyglutamate hydrochloride (6)

3-Hydroxyglutamic acid was prepared according to the procedure of Vidal-Cros, Gaudry and Marquet as described in the Journal of Organic Chemistry 50:3163 (1985). In a round-bottomed flask 8.0 g (~50 mmol) of powdered 3-hydroxyglutamic acid was suspended in 250 ml of dry methanol and the mixture cooled to 0° C. with the aid of an ice bath. Thionylchloride (25 ml) was slowly added to the solution and when the addition was complete, the ice bath was removed and the solution was allowed to stir for 18 hours at 25° C. It was then refluxed for four hours, 200 ml of benzene was added and evaporated under reduced pressure to dryness. The resultant residue was dissolved in 100 ml of acetone and with the slow addition of diethyl ether and trituration crystals were formed. These crystals were separated by filtration, washed with 50 ml ether followed by 15 ml of acetone and dried in a vacuum over $P_2O_5$: yield 58%; mp 137°-138° C.; NMR (TFA) δ4.75 (br, d, 1H, αH), 3.79, 3.65 (s, s, 3H, 3H, carbomethoxy), 2.82 (d, 2H, —CH$_2$—); mass spectrum, calculated for $C_7H_{13}NO_4$, (MH+) 192, found 192.

4-Amino-4-deoxy-10-methylpteroyl-β-hydroxyglutamic acid (2)

In a glass stoppered measuring cylinder 326 mg (1 mmole) of 4-amino-4-deoxy-10-methyl pteroic acid (3) purchased from Aldridh Chemical company was dissolved in 100 ml of dry DMF at 80° C., and 0.28 ml (2 mmol) of triethylamine was added. After cooling the solution to 0° C. in an ice bath, 0.262 ml of freshly distilled isobutylchloroformate was added and the solution kept at this temperature for 90 minutes with occasional shaking. The reaction mixture was removed from the ice bath and set aside at 25° C. for 30 minutes. A solution of 6 (456 mg, 2 mmol) in 15 ml of DMF was neutralized with 0.28 ml of triethylamine and it was added immediately to the above mixed anhydride solution and stirred for 18 hours at 25° C. The reaction mixture was evaporated to dryness at 55° C. under reduced pressure, and stirred with a mixture of 10 ml of 5% NaHCO$_3$ and 10 ml of ether for 1 hour. The suspension was filtered and the residue washed with water and hydrolyzed with a mixture of 80 ml of 0.1N NaOH and 25 ml of acetonitrile for 18 hours at 25° C. After removal of the acetonitrile under reduced pressure, the pH of the solution was adjusted to 7.5 with 1N HCl, diluted to 800 ml with distilled water and applied on a DEAE-cellulose column (chloride form). The product was eluted from the column using a linear NaCl gradient from 0.0–0.5M in 0.005M phosphate buffer at pH 7.0. Fractions corresponding to the desired product (2) were pooled and the pH was adjusted to 3.5 with glacial HOAc. On refrigeration, a yellow precipitate of 2 formed. This was filtered, washed and dried in a vacuum over $P_2O_5$. Yield, 180 mg (40%); mp 238°-241° C. (dec). NMR (TFA) δ2.75 (c, 2H, γ—CH$_2$), 3.28 (s, 3H, —NCH$_3$), 4.51 (c, 1H, —CHOH), 4.8 (c, 1H, α—CH), 5.0 (s, 2H, —CH$_2$—N—Me), 7.65 (q, 4H, aromatic), 851 (s, 1H, C$_7$H).

4-Amino-10-methylpteroyl-β-hydroxyglutamic acid (2) analyzed as follows:

| Mol formula | Mol wt (calcd) | (found) | 0.1 N NaOH max nm (ε) |
|---|---|---|---|
| $C_{20}H_{22}N_8O_6$ | 470 | 470 | 256 (23,880)<br>368 ( 7,986) |

The glutamate compounds 1 or 2 can be used as such or in the form of salts that are formed with one or more amino groups of the pteridine ring. Acids such as hydrochloric, hydrobromic, sulfonic, nitric, phosphoric, and organic carboxylic acids such as maleic, citric, salicylic and methane sulfonic acid may be used for the preparation of the addition salts.

The glutamate compounds 1 or 2 or salts thereof may be administered to a warm-blooded animal by oral and parenteral (intraperitoneal, intravenous, intrathecal, subcutaneous, intramuscular) administration. A dosage of 1 or 2 in the amount of 0.1 mg to about 500 mg/kg to ameliorate the leukemia, ascites or solid tumors or rheumatoid arthritis in humans will be sufficient. The higher dosage amount of about 500 mg/kg may be administered in conjunction with leucovorin (6(RS) 5-formyl-tetrahydro-folate) to further reduce toxicity. To ameliorate rheumatoid arthritis in humans, a dosage range of 0.01 mg to 10 mg/day will be sufficient.

The glutamate compounds 1 or 2 can be provided in composite forms to facilitate administration or in dosage unit form. A sterile and nontoxic carrier may be added to 1 or 2; the carrier may be a liquid, solid, or semisolid which may serve as a vehicle, medium or excipient. The carriers may include gelatin, methylcellulose, propylhydroxybenzoate, talc, magnesium stearate, oil of theobroma, gum aracia, lactose, dextrose, mannitol, sorbitol and mineral oil. The glutamate compounds 1 or 2 and carrier or diluent can be enclosed or encapsulated in a paper or other container, capsule, cachet, gelatin, or sachet when intended for use in dosage units. The dosage units can take the form of cachets, suppositories, capsules or tablets.

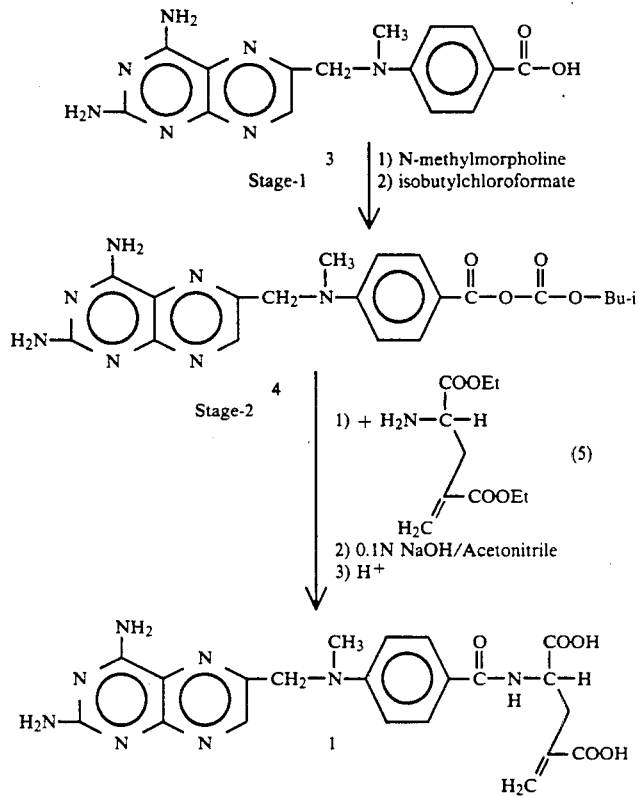

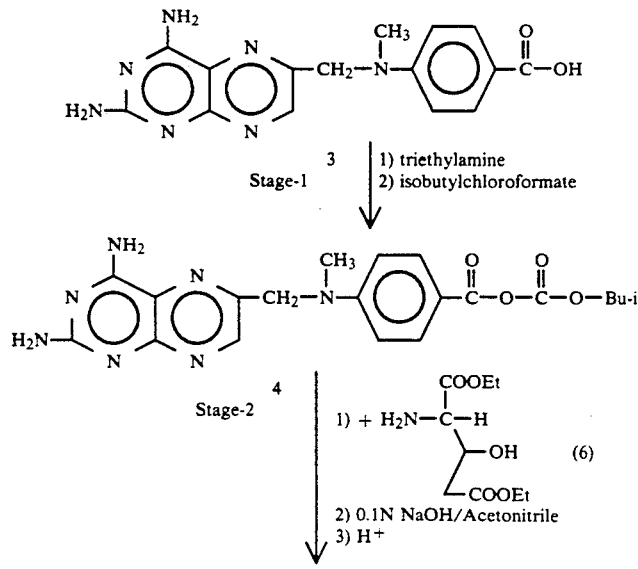

-continued

Scheme-2
Steps of the reaction synthesis of 4-amino-4-
deoxy-10-methylpteroyl- -hydroxyglutamic acid (2).

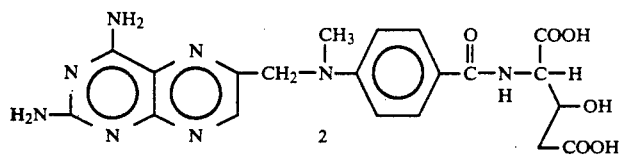

TABLE I
INHIBITION OF TUMOR CELL GROWTH BY 1 AND 2

| Compound | I$_{50}$ (nM)* | | |
|---|---|---|---|
| | H35 hepatoma | Human Manca lymphoid leukemia | CCRF-CEM human leukemia |
| 1 | 8.0 | 13.0 | 15.0 |
| 2 | 42.0 | 24.0 | |
| Methotrexate | 10.0 | 6.0 | 12.0 |

Manca cell growth assay was performed as described by Thorndike, Gaumont, Kisliuk, Sirotnak, Murthy and Nair in Cancer Research 49:158 (1989). Growth inhibition of H35-hepatoma cells was measured as described by Patil, Jones, Nair, Gali van, Maley, Kisliuk, Gaumont, Duch and Ferone in the Journal of Medicinal Chemistry 32:1284 (1989) and that of CCRF-CEM human leukemia cells according to the procedures of McGuire, Graber, Licato, Vincenz, Coward, Nimec and Galivan (Cancer Research 49:4517, 1989).
*Corrected for the presence of the D-enantiomer of τ-methyleneglutamate. The values correspond to duplicate experiments.

TABLE II
INHIBITION OF RECOMBINANT HUMAN DIHYDROFOLATE REDUCTASE BY 1 AND 2

| Compound | IC$_{50}$ (nM) |
|---|---|
| 1 | 5.4 |
| 2 | 5.3 |
| Methotrexate | 3.9 |

Pure human dihydrofolate reductase from lymphoblastoid cells were used. The enzymatic assay was performed as described by Pastore, Plante and Kisliuk in Methods in Enzymology 34:281 (1974). The enzyme concentration in the assay was $8 \times 10^{-9}$ M.

TABLE III
INHIBITION OF FOLINIC ACID TRANSPORT TO H35 HEPATOMA CELLS BY COMPOUND 1 AND METHOTREXATE

| Compound | I$_{50}$ (nM)* |
|---|---|
| Methotrexate | 18.00 |
| 1 | 3.5 |

Transport experiments were conducted as described by Patil, Jones, Nair, Galivan, Maley, Kisliuk, Gaumont, Duch and Merone in the Journal of Medicinal Chemistry 32:1284 (1989). Folinic acid (2 μM, 15 min uptake).
*Corrected for the presence of the D-isomer of τ-methyleneglutamate

TABLE IV
SUBSTRATE ACTIVITY OF 4-AMINO-4-DEOXY-10-METHYLPTEROYL-τ-METHYLENEGLUTAMIC ACID (1) AND 4-AMINO-4-DEOXY-10-METHYLPTEROYL-β-HYDROXYGLUTAMIC ACID (2) TOWARDS CCRF-CEM HUMAN LEUKEMIA CELL FOLYLPOLYGLUTAMATE SYNTHETASE (FPGS)

| | Conc (μM) | Substrate activity |
|---|---|---|
| Compound | | |
| 1 | 50 | 3.5 |
| 2 | 50 | 1.8 |
| Controls | | |
| Aminopterin | 50 | 950 |
| 10-Deazaaminopterin | 50 | 1020 |

The assays were performed as described by McGuire, Graber, Licato, Vincenz, Coward, Nimec and Galivan in Cancer Research 49:4517 (1989).

Having regard to the foregoing disclosure, the following is claimed as inventive and patentable embodiments thereof.

1.

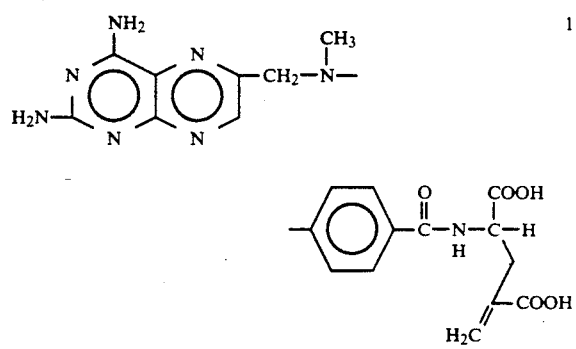

2.

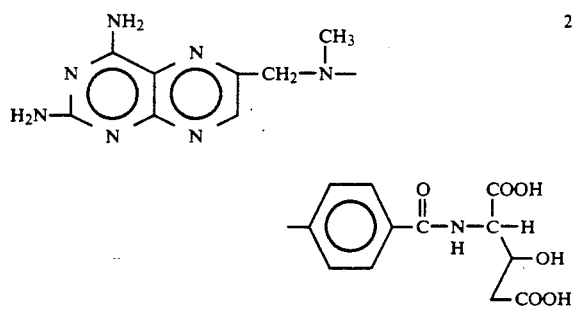

3. A pharmaceutical composition in dosage unit form for treating leukemia, ascites tumors or solid tumors comprising an amount within the range of about 0.1 to about 500 mg of 4-amino-4-deoxy-10-deazapteroyl-τ-methyleneglutamic acid per dosage unit therapeutically effective to ameliorate leukemia, ascites tumors or solid tumors together with a pharmaceutically acceptable nontoxic carrier or diluent thereof.

4. A pharmaceutical composition in dosage unit form for treating leukemia, ascites tumors or solid tumors comprising an amount within the range of about 0.1 to about 500 mg of 4-amino-4-deoxy-10-methylpteroyl-3-hydroxyglutamic acid per dosage unit therapeutically effective to ameliorate leukemia, ascites tumors or solid tumors together with a pharmaceutically acceptable nontoxic carrier or diluent thereof.

5. A process for treating leukemia, ascites tumors or solid tumors which comprises administering orally or parenterally to a warm-blooded animal having an abnormal proportion of leukocytes or other evidence of malignancy, a therapeutic and relatively nontoxic amount of 4-amino-4-deoxy-10-methylpteroyl-τ- methyleneglutamic acid to ameliorate leukemia, ascites tumors or solid tumors.

6. A process for treating leukemia, ascites tumors or solid tumors which comprises administering orally or parenterally to a warm-blooded animal having an abnormal proportion of leukocytes or other evidence of malignancy, a therapeutic and relatively nontoxic amount of 4-amino-4-deoxy-10-methylpteroyl-3-hydroxyglutamic acid to ameliorate leukemia, ascites tumors or solid tumors.

* * * * *